United States Patent [19]

Schmitt et al.

[11] Patent Number: 4,545,994
[45] Date of Patent: Oct. 8, 1985

[54] TRIHALOALLYL THIOCYANATES, A PROCESS FOR THEIR PREPARATION AND THEIR USE IN MICROBICIDAL AGENTS

[75] Inventors: Hans-Georg Schmitt, Leverkusen; Wilfried Paulus; Hermann Genth, both of Krefeld, all of Fed. Rep. of Germany

[73] Assignee: Bayer Aktiengesellschaft, Leverkusen, Fed. Rep. of Germany

[21] Appl. No.: 670,173

[22] Filed: Nov. 13, 1984

[30] Foreign Application Priority Data

Nov. 17, 1983 [DE] Fed. Rep. of Germany ....... 3341556

[51] Int. Cl.$^4$ .................. A01N 47/46; C07C 161/02
[52] U.S. Cl. .................................... 514/514; 260/454
[58] Field of Search ........................ 260/454; 424/302

[56] References Cited

U.S. PATENT DOCUMENTS 3,212,963 10/1965 Wehner .............................. 260/454
4,087,451 5/1978 Merianus ............................ 260/454

FOREIGN PATENT DOCUMENTS 895186 5/1962 United Kingdom ................ 260/454

*Primary Examiner*—Alan Siegel
*Attorney, Agent, or Firm*—Sprung, Horn, Kramer & Woods

[57] ABSTRACT

New trihaloallyl thiocyanates of the formula

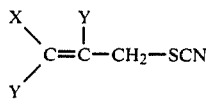

in which X and Y are identical or different and denote chlorine, bromine or iodine, can be prepared by reacting trihaloallyl compounds

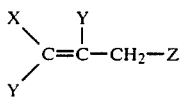

in which
X and Y are identical or different and denote chlorine, bromine or iodine and
Z represents a nucleofugic group,
with thiocyanates. The new compounds are active compounds in microbicidal agents.

16 Claims, No Drawings

TRIHALOALLYL THIOCYANATES, A PROCESS FOR THEIR PREPARATION AND THEIR USE IN MICROBICIDAL AGENTS

The invention relates to new trihaloally thiocyantes, a process for their preparation and their use in microbicidal agents.

New trihaloallyl thiocyanates of the formula

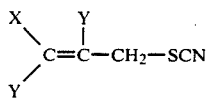

in which X and Y are identical or different and denote chlorine, bromine or iodine, have been found.

The new trihaloallyl thiocyanates have, as active compounds in microbicidal agents, an outstanding action which was not to be expected.

Preferred trihaloallyl thiocyanates are compounds of the formula

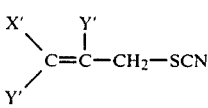

in which
X' represents bromine, chlorine or iodine and
Y' represents bromine or iodine.

The following trihaloallylthiocyanates may be mentioned as examples: 2,3,3-triiodoallyl thiocyanate, 2,3-dibromo-3-chloro-allyl thiocyanate, 2,3-diiodo-3-chloro-allyl thiocyanate, 2,3,3-tribromo-allyl thiocyanate, 2,3-diiodo-3-bromo-allyl thiocyanate, 2,3-dibromo-3-iodoallyl thiocyanate, 2,3,3-trichloroallyl thiocyanate, 2,3-dichloro-3-bromo-allyl thiocyanate and 2,3-dichloro-3-iodo-allyl thiocyanate.

According to the invention, examples of preferred trihaloallyl thiocyanates are 2,3,3-triiodoallyl thiocyanate, 2,3-dibromo-3-iodo-allyl thiocyanate, 2,3,3-tribromo-allyl thiocyanate, 2,3-diiodo-3-chloro-allyl thiocyanate and 2,3-diiodo-3-bromo-allyl thiocyanate.

A process has also been found for the preparation of the new trihaloally thiocyanates, which is characterized in that trihaloallyl compounds of the formula

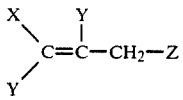

in which
X and Y are identical or different and denote chlorine, bromine or iodine and
Z represents a nucleofugic group,
are reacted with a thiocyanate of the formula

in which M denotes an alkali metal or ammonium.

The process according to the invention can be illustrated, for example, with the aid of the following equation:

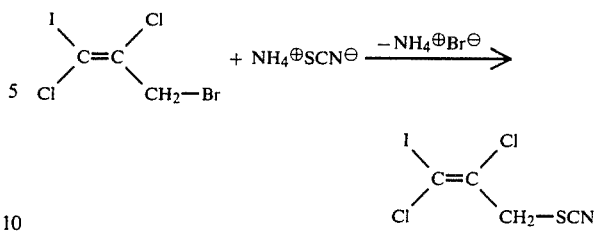

Alkali metal in the context of the process according to the invention is understood as meaning metals of the first group of the Mendeleev periodic table. Examples which may be mentioned are lithium, sodium, potassium, rubidium and caesium, preferably sodium and potassium.

According to the invention, a nucleofugic group is understood as meaning an atom or a group of atoms which, because of its ability to stabilize negative charges, facilitates substitution reactions on the saturated carbon atom.

Examples of nucleofugic groups are halogens, such as fluorine, chlorine, bromine and iodine, preferably chlorine and bromine, alkylsulphonyloxy groups, such as methylsulphonyloxy and ethylenesulphonyloxy, and arylsulphonyloxy, such as phenylsulphonyloxy and 4-tolylsulphonyloxy.

The trihaloallyl derivatives used as starting compounds are known in some cases from Japanese Patent No. 82, 112,303 and C.A. 97, 177 037 (1982), and they can be prepared by processes which are known per se. Thus, for example, trihaloallyl halides can be obtained by halogenation of halopropargyl halides. Sulphonic acid trihaloallyl esters are obtained by reacting trihaloallyl alcohols with sulphonic acid chlorides.

The following trihaloallyl derivatives may be mentioned as examples: 3-chloro-2,3-diiodoallyl chloride, 3-bromo-2,3-diiodoallyl bromide, 2,3,3-triiodoallyl chloride, 2,3,3-tribromoallyl bromide, 2,3-dibromo-3-iodoallyl chloride and 2,3-dichloro-3-iodoallyl bromide.

The preferred thiocyanates for the process according to the invention are sodium thiocyanate, potassium thiocyanate and ammonium thiocyanate.

If appropriate, the process according to the invention can be carried out in the presence of a solvent or diluent. Polar solvents or diluents which do not change under the reaction conditions are in general used as the solvent or diluent. The following solvents and diluents may be mentioned as examples: water, alcohols, such as methanol and ethanol, ethers, such as dioxane or tetrahydrofuran, ketones, such as acetone, amides, such as dimethylformamide, and nitriles, such as acetonitrile.

The process according to the invention is in general carried out in the temperature range from $-20°$ C. to $100°$ C., preferably in the range from $0°$ C. to $60°$ C.

The process according to the invention is in general carried out under normal pressure. However, it can also be carried out under an increased or reduced pressure.

The components of the process according to the invention are usually employed in equimolar amounts.

To accelerate the reaction, it may be advantageous to add a catalyst, such as sodium iodide, to the reaction. In general, 0.0001 to 0.2, preferably 0.001 to 0.05, part by weight of the catalyst, based on the trihaloallyl derivative, are added to the reaction.

The process according to the invention can be carried out, for example, as follows. If appropriate, the thiocyanate is dissolved or suspended in a solvent, and the trihaloallyl derivative is added. The reaction mixture is stirred at the desired reaction temperature, if appropriate in the presence of a catalyst.

When the reaction has ended, the trihaloallyl thiocyanates according to the invention are obtained in a manner which is known per se by concentration, removal of the salt formed, recrystallization or reprecipitation.

The trihaloallyl thiocyanates according to the invention can be used as active compounds for combating microorganisms, preferably in industrial materials.

According to the invention, industrial materials are non-living materials which have been prepared for use in industry. Industrial materials which are to be protected by the active compound according to the invention from microbial change or destruction are, for example, adhesives, sizes, paper and card, textiles, leather, wood, paints and articles made of plastic, cooling lubricants and other materials which can be destroyed by microorganisms. Components of production plants, for example cooling water circulations, which can be affected by microorganisms may also be mentioned in the context of materials to be protected. Industrial materials which may be mentioned as preferred in the context of the present invention are adhesives, sizes, paper and card, leather, wood, paints, cooling lubricants and cooling circulations.

Examples which may be mentioned of microorganisms which can cause degradation of or change to the industrial materials are bacteria, yeasts, algae and slime organisms. Preferably the active compounds according to the invention are effective against bacteria, fungi which discolour and destroy wood (Basidiomycetes), and against slime organisms and algae. Microorganisms of the following genera may be mentioned as examples: Alternaria, such as *Alternaria tenuis,* Aspergillus, such as *aspergillus niger,* Chaetomium, such as *Chaetomium globosum,* Coniophora, such as *Coniophora puteana,* Lentinus, such as *Lentinus tigrinus,* Penicillium, such as *Penicillium glaucum,* Polyporus, such as *Polyporus versicolor,* Aureobasidium, such as *Aureobasidium pullulans,* Sclerophoma, such as *Sclerophoma pityophila,* Staphylococcus, such as *Staphylococcus aureus,* Pseudomonas, such as *Pseudomonas aeruginosa,* Escherichia, such as *Escherichia coli,* and furthermore green algae, blue algae and diatoms.

The active compounds according to the invention can be converted into the customary formulations, such as solutions, emulsions, suspensions, powders, pastes and granules, depending on their field of application.

These formulations can be prepared in a manner which is known per se, for example by mixing the active compounds with an extender which consists of liquid solvent and/or solid carriers, if appropriate using surface-active agents, such as emulsifiers and/or dispersing agents, it being possible for example in the case of the use of aqueous extenders, for organic solvents, such as alcohols, to be used as auxiliaries if necessary.

Organic solvents for the active compounds can be, for example, alcohols, such as lower aliphatic alcohols, preferably ehtanol or isopropanol, or benzyl alcohol, ketones, such as acetone or methyl ethyl ketone, liquid hydrocarbons, such as benzine fractions, and halogenated hydrocarbons, such as 1,2-dichloroethane.

The microbicidal agents according to the invention in general contain the active compound in an amount of 0.5 to 95 parts by weight, preferably of 1 to 50% by weight.

The use concentration of the active compounds according to the invention depends on the nature and the occurrence of the microorganisms to be combated, and on the composition of the material to be protected. The optimum amount to be used can be determined by test series.

The use concentrations are in general in the range from 0.001 to 5% by weight, preferably from 0.01 to 0.5% by weight, based on the material to be protected.

The new active compounds according to the invention can also be mixed with other known active compounds. The following active compounds may be mentioned as examples: benzyl alcohol mono(poly)hemiformal, benzimidazolyl methylcarbamate, tetramethyl-thiuram disulphide, zinc salts of dialkyl dithiocarbamates, 2,4,5,6-tetrachloroisophthalonitrile, thiazolyl benzimidazole, mercapto benzthiazole and phenol derivatives, such as 2-phenyl-phenol, (2,2'-dihydroxy-5,5'-dichloro)-diphenylmethane and 3-methyl-4-chloro-phenol.

PREPARATION EXAMPLES

EXAMPLE 1

2,3,3-Triiodoallyl thiocyanate 9.14 g (0.113 mole) of sodium thiocyanate are dissolved in 200 ml of acetone; 51.4 g (0.113 mole) of 3-chloro-1,1,2-triiodo-1-propene are then added. In addition, 0.2 g of sodium iodide are also introduced as the catalyst. The reaction mixture is stirred at room temperature for 12 hours.

When the reaction has ended, the reaction mixture is concentrated on a rotary evaporator, the residue is stirred into 500 ml of water and the solid precipitate is filtered off with suction and dried in a desiccator.

51 g (94.6% of theory) of light beige crystals of melting point 62° to 63° C.

IR: $\nu_{SCN}$ 2145 and 2160 cm$^{-1}$.

NMR: δ(CDCl$_3$) 4.25 ppm.

The following compounds are obtained analogously:

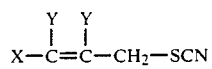

| Example No. | X | Y | Melting point (°C.) | Yield (%) | $^1$H—NMR δ(CDCl$_3$)CH$_2$ (ppm) | IR γSCN (cm$^{-1}$) |
|---|---|---|---|---|---|---|
| 2 | Cl | Br | 38 | 82.3 | 4.22 | 2160 |
| 3 | Cl | I | 54–55 | 86.5 | 4.23 | 2152 |
| 4 | Br | Br | 43–44 | 98.5 | 4.21 | 2158 |
| 5 | Br | I | 44–45 | 99.0 | 4.20 | 2158 |
| 6 | I | Br | 60–62 | 65.3 | 4.30 | 2158 |

USE EXAMPLES

EXAMPLE 7

The minimum inhibitory concentrations (MIC) of active compounds according to the invention are determined to demostrate the activity against fungi:

Active compounds according to the invention are added in concentrations of 0.1 mg/liter to 5,000 mg/liter to an agar prepared from beerwort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentration of active compound at which no growth at all of the species of microbe used takes place, and is shown in the following Table 1.

TABLE 1

MIC's in mg/l for the action of substances according to the invention on fungi

| Test organisms | according to Example | Substance 1 | 2 | 3 | 4 | 5 | 6 |
|---|---|---|---|---|---|---|---|
| *Alternaria tenuis* | 2 | | | | | | 5 |
| *Aspergillus niger* | 3.5 | 50 | <20 | 50 | <20 | 20 | |
| *Aureobasidium pullulans* | 1 | | | | | | 5 |
| *Chaetomium globosum* | 5 | 50 | <20 | 50 | <20 | 35 | |
| *Coniophora puteana* | 0.5 | | | | | | 1 |
| *Lentinus tigrinus* | 0.5 | | | | | | 10 |
| *Penicillium glaucum* | 2 | 50 | <20 | 50 | <20 | 10 | |
| *Polyporus versicolor* | 0.5 | | | | | | 5 |
| *Sclerophoma pityophila* | 0.5 | | | | | | 2 |
| *Trichoderma viride* | 5 | | | | | | 20 |

EXAMPLE 8

(Action against bacteria)

The active compounds shown in Table 2 are added in concentrations of 1 to 5,000 mg/liter to an agar containing broth as the nutrient medium. Thereafter, the nutrient medium is infected either with *Escherichia coli* or with *Staphylococcus aureus* and the infected medium is kept at 28° C. and 60 to 70% relative atmospheric humidity for 2 weeks. The MIC is the lowest concentration of active compound at which no growth at all of the species of microbe used takes place.

The MIC values are shown in Table 2.

TABLE 2

MIC value data in mg/liter for the action of the active compounds shown below on bacteria.

| Test organisms | Active compounds according to Example |  |  |  |  |  |
|---|---|---|---|---|---|---|
| | 1 | 2 | 3 | 4 | 5 | 6 |
| *Escherichia coli* | 35 | 100 | 100 | 100 | 50 | 100 |
| *Staphylococcus aureus* | <20 | <50 | <20 | <50 | <20 | <20 |

EXAMPLE 9

(Action against slime organisms)

Substances according to the invention are used in concentrations of in each case 0.1 to 100 mg/liter in Allens nutrient solution (Arch. Mikrobiol. 17, 34 to 53 (1952)), which contains 0.2 g of ammonium chloride, 4.0 g of sdium nitrate, 1.0 g of dipotassium hydrogen phosphate, 0.2 g of calcium chloride, 2.05 g of magnesium sulphate, 0.02 g of iron chloride and 1% of caprolactam in 4 liters of sterile water, dissolved in a little acetone. Shortly beforehand, the nutrient solution is infected with slime organisms (about $10^6$ germs/ml) which have been isolated from the spinning water circulation used in the production of polyamide. Nutrient solutions which contain the minimum inhibitory concentration (MIC) or larger active compound concentrations are still completely clear after culture for 3 weeks at room temperature, that is to say the multiplication of the microbes and slime formation noticeable after 3 to 4 days in nutrient solutions containing no active compound are absent.

TABLE 3

MIC values in mg/liter for the action of the substances shown below on slime organisms

| Active compound according to Example | MIC in mg/liter |
|---|---|
| 1 | 0.75 |
| 6 | 3.5 |

EXAMPLE 10

A mixed culture of green algae, blue algae, brown algae and diatoms (*Stichococcus bacillaris* Naegeli, *Euglena gracilis* Klebs, *Chlorella pyrenoidosa* Chick, *Phormidium foveolarum* Gomont, *Oscillatoria geminata* Meneghini and *Phaeodactylum tricornutum* Bohlin) is introduced into Allens nutrient solution (Arch. Mikrobiol. 17, 34 to 53 (1952)), which contains 0.2 g of ammonium chloride, 4.0 g of sodium nitrate, 1.0 g of dipotassium hydrogen phosphate, 0.2 g of calcium chloride, 2.05 g of magnesium sulphate and 0.02 g of iron chloride and 1% of caprolactam in 4 liters of sterile water, while bubbling through air. After 2 weeks, the nutrient solution is coloured deep green-blue as a result of intensive algal growth. Dying off of the algae after addition of active compounds according to the invention can be seen from the decolorization of the nutrient solution.

TABLE 4

Algae-destroying concentrations (mg/liter) of the substances shown below

| Active compound according to Example | Destroying concentrations in mg/liter |
|---|---|
| 1 | 35 |
| 6 | 50 |

What is claimed is:

1. A trihaloallyl thiocyanate of the formula

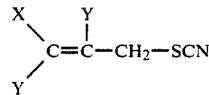

wherein X and Y are identical or different and denote chlorine, bromine or iodine.

2. A compound according to claim 1 wherein X is chlorine and Y is bromine.

3. A compound according to claim 1 wherein X is chlorine and Y is iodine.

4. A compound according to claim 1 wherein X and Y are bromine.

5. A compound according to claim 1 wherein X is bromine and Y is iodine.

6. A compound according to claim 1 wherein X is iodine and Y is bromine.

7. A compound according to claim 1 which is 2,3,3-triiodoallyl thiocyanate.

8. A microbicidal composition which comprises a trihaloallyl compound of the formula

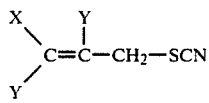

wherein X and Y are identical or different and denote chlorine, bromine or iodine and a microbicidally compatible diluent.

9. A composition according to claim 8 wherein said trihaloallyl compound is triiodoallyl thiocyanate.

10. A composition according to claim 8 wherein X is chlorine and Y is bromine.

11. A composition according to claim 8 wherein X is chlorine and Y is iodine.

12. A composition according to claim 8 wherein X and Y are bromine.

13. A composition according to claim 8 wherein X is bromine and Y is iodine.

14. A composition according to claim 8 wherein X is iodine and Y is bromine.

15. A process for rendering an industrial material less susceptible to microbial attack which comprises applying to said industrial material a microbicidally effective amount of a trihaloallyl compound of the formula

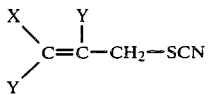

wherein X and Y are identical or different and denote chlorine, bromine or iodine.

16. A process according to claim 15 wherein said trihaloallyl compound is applied to said industrial material in an amount of 0.001 to 5 percent by weight, based on the weight of said industrial material.

* * * * *